US012582367B2

(12) United States Patent
Yoshida et al.

(10) Patent No.: US 12,582,367 B2
(45) Date of Patent: Mar. 24, 2026

(54) X-RAY DIAGNOSTIC DEVICE AND MEDICAL COUCH DEVICE COMPRISING A COUCHTOP, A DRIVE MECHANSM, A CONSOLE, AND PROCESSING CIRCUITRY

(71) Applicant: CANON MEDICAL SYSTEMS CORPORATION, Tochigi (JP)

(72) Inventors: Hiroshi Yoshida, Yaita (JP); Keisuke Sugawara, Otawara (JP); Katsuaki Shinoda, Shioya (JP); Hisayasu Yumiza, Otawara (JP); Kazuo Imagawa, Nasushiobara (JP); Ritsu Yokohama, Nasushiobara (JP)

(73) Assignee: CANON MEDICAL SYSTEMS CORPORATION, Tochigi (JP)

( * ) Notice: Subject to any disclaimer, the term of this patent is extended or adjusted under 35 U.S.C. 154(b) by 216 days.

(21) Appl. No.: 18/530,312

(22) Filed: Dec. 6, 2023

(65) Prior Publication Data

US 2024/0188907 A1 Jun. 13, 2024

(30) Foreign Application Priority Data

Dec. 7, 2022 (JP) ................................. 2022-195840
Dec. 4, 2023 (JP) ................................. 2023-204967

(51) Int. Cl.
*A61B 6/04* (2006.01)
*A61B 6/00* (2006.01)
*A61B 6/46* (2024.01)

(52) U.S. Cl.
CPC .......... *A61B 6/0487* (2020.08); *A61B 6/0407* (2013.01); *A61B 6/4441* (2013.01);
(Continued)

(58) Field of Classification Search
CPC ....... A61B 6/04; A61B 6/0407; A61B 6/0487; A61B 6/44; A61B 6/4429; A61B 6/4435;
(Continued)

(56) References Cited

U.S. PATENT DOCUMENTS 5,740,222 A * 4/1998 Fujita ..................... A61B 6/548
378/4
6,045,262 A * 4/2000 Igeta ................... A61B 6/0487
378/209
(Continued)

FOREIGN PATENT DOCUMENTS

JP 11-137543 A 5/1999

*Primary Examiner* — Allen C. Ho
(74) *Attorney, Agent, or Firm* — Oblon, McClelland, Maier & Neustadt, L.L.P.

(57) ABSTRACT

An X-ray diagnostic device according to embodiments includes an X-ray tube, an X-ray detector, a couchtop, a drive mechanism, an input interface, and processing circuitry. The X-ray tube emits X-rays to a subject. The X-ray detector detects X-rays transmitted through the subject. The couchtop has the subject placed thereon. The drive mechanism generates the driving force for moving the couchtop. The input interface accepts instruction operations from an operator regarding the movement of the couchtop. The processing circuitry acquires one of a weight applied to the couchtop and a deflection amount of the couchtop, and determines the driving force to be generated by the drive mechanism based on one of the weight and the deflection amount and on the instruction operation.

20 Claims, 13 Drawing Sheets

(52) U.S. Cl.
CPC ................ *A61B 6/467* (2013.01); *A61B 6/54*
(2013.01); *A61B 6/542* (2013.01); *A61B 6/545*
(2013.01)

(58) Field of Classification Search
CPC ....... A61B 6/4441; A61B 6/4447; A61B 6/46;
A61B 6/461; A61B 6/467; A61B 6/54;
A61B 6/542; A61B 6/462; A61B 6/545
USPC ............................... 5/601; 378/62, 208, 209
See application file for complete search history.

(56) References Cited

U.S. PATENT DOCUMENTS

| | | | | |
|---|---|---|---|---|
| 6,522,713 | B1 * | 2/2003 | Valiga .................... | A61B 6/032 |
| | | | | 378/4 |
| 7,682,079 | B2 * | 3/2010 | Schwartz ............... | A61B 5/055 |
| | | | | 378/209 |
| 8,683,628 | B2 * | 4/2014 | Baumann ............... | A61B 5/704 |
| | | | | 5/616 |
| 9,462,981 | B2 * | 10/2016 | Padwa ................. | A61B 6/0492 |
| 10,448,916 | B2 * | 10/2019 | Tahara .................... | A61B 6/588 |
| 10,607,809 | B2 * | 3/2020 | Adachi .................... | A61B 6/04 |
| 11,202,611 | B2 * | 12/2021 | Magari .................. | A61B 6/467 |
| 11,337,666 | B2 * | 5/2022 | Yoshida ............... | A61B 6/0407 |
| 11,540,795 | B2 * | 1/2023 | Kobayashi ........... | A61B 6/0407 |
| 11,627,927 | B2 * | 4/2023 | Hoecht ............... | A61B 6/0407 |
| | | | | 700/83 |

* cited by examiner

| OPERATOR ID | MOTOR ASSIST AMOUNT CALCULATION ALGORITHM |
|---|---|
| AA | MOTOR ASSIST AMOUNT CALCULATION ALGORITHM A |
| BB | MOTOR ASSIST AMOUNT CALCULATION ALGORITHM B |
| ... | ... |

X-RAY DIAGNOSTIC DEVICE AND MEDICAL COUCH DEVICE COMPRISING A COUCHTOP, A DRIVE MECHANSM, A CONSOLE, AND PROCESSING CIRCUITRY

CROSS-REFERENCE TO RELATED APPLICATIONS

This application is based upon and claims the benefit of priority from Japanese Patent Application No. 2022-195840, filed on Dec. 7, 2022 and Japanese Patent Application No. 2023-204967, filed on Dec. 4, 2023; the entire contents of which are incorporated herein by reference.

FIELD

Embodiments described herein relate generally to an X-ray diagnostic device and a medical couch device.

BACKGROUND

Conventionally, a medical diagnostic imaging device such as an X-ray diagnostic device for circulatory organs is equipped with a couch device that has a couchtop on which a subject such as a patient is placed. Furthermore, the couch device is equipped with a mechanism to move the couchtop in a horizontal direction manually or electrically. For example, in an X-ray diagnostic device, panning operations are performed to change the position of the couchtop in the longitudinal direction as well as the position of the couchtop in the lateral direction. In this manner, an operator changes the field of view of the surgical area by moving the desired site of the subject into the X-ray irradiation area, and inserts and removes devices used for treatment.

For example, when changing the position of the couchtop in the longitudinal direction or the lateral direction, the operator manually moves the couchtop to the target position while pressing a brake release switch (panning knob) provided on a console of the couch device. Furthermore, for example, the operator electrically moves the couchtop to the target position by operating the console or a remote control.

Note here that the load in the direction of gravity on the couchtop increases due to various factors. For example, the load in the direction of gravity on the couchtop increases in a state where a subject is placed on the couchtop or in a state where other modality devices such as other consoles, tablets, or injectors are attached to side rails of the couch device. Therefore, the operator needs a large operating force when moving the couchtop manually. In particular, a large operating force is required when starting or stopping the movement of the couchtop.

In addition, when the operator moves the couchtop electrically, it is difficult for the operator to perform fine positioning as precisely as the operator wishes since the feeling of control is smaller than the case of moving the couchtop manually.

DETAILED DESCRIPTION

One of the issues that embodiments described herein are to solve is to improve the operability of operations for moving a couchtop. Note, however, that the issues to be solved by the embodiments described herein are not limited to the above issue. Issues related to the effects of the configurations indicated in the embodiments described below can also be positioned as other issues.

An X-ray diagnostic device according to the embodiments includes an X-ray tube, an X-ray detector, a couchtop, a drive mechanism, an input interface, and processing circuitry. The X-ray tube emits X-rays to a subject. The X-ray detector detects X-rays transmitted through the subject. The couchtop has the subject placed thereon. The drive mechanism generates the driving force for moving the couchtop. The input interface accepts instruction operations from an operator regarding the movement of the couchtop. The processing circuitry acquires one of the weight applied to the couchtop and the deflection amount of the couchtop, and determines the driving force to be generated by the drive mechanism based on one of the weight and the deflection amount and on the instruction operation.

Hereinafter, the X-ray diagnostic device and a medical couch device according to each of the embodiments will be described with reference to the accompanying drawings. Note that contents described in one of the embodiments and one of modification examples are, in principle, applicable to the other embodiments and other modification examples as well, as long as there is no contradiction.

First Embodiment

Figure 1:
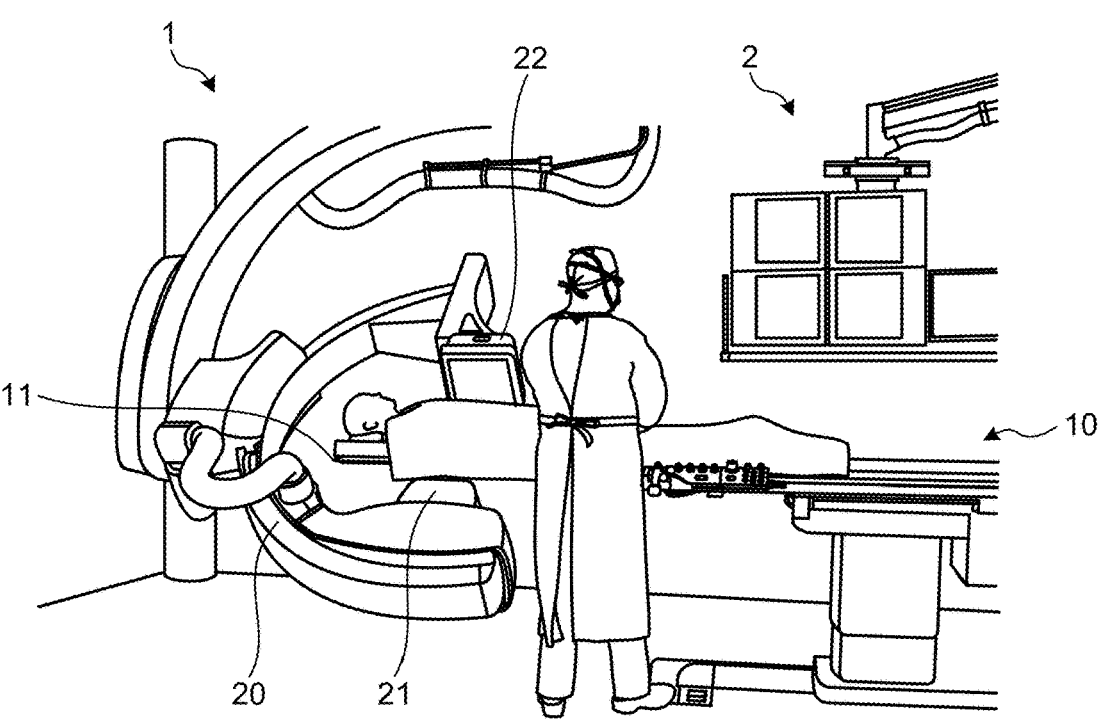
FIG. 1 is an explanatory diagram for describing an example of an X-ray diagnostic device according to a first embodiment.

FIG. 1 is an explanatory diagram for describing an example of an X-ray diagnostic device 1 according to the first embodiment. The X-ray diagnostic device 1 illustrated in FIG. 1 includes a couch device 10, a C-type arm 20, and a display device 2. The couch device 10 includes a couchtop 11 on which a subject such as a patient is placed. The couch device 10 is an example of the medical couch device.

The C-type arm 20 includes an X-ray tube 21 and an X-ray detector 22. The X-ray tube 21 and the X-ray detector 22 are imaging mechanisms for capturing images of the subject. The X-ray tube 21 emits X-rays to the subject. The X-ray detector 22 detects X-rays transmitted through the subject. The X-ray detector 22 converts the detected X-rays into electrical signals. The X-ray diagnostic device 1 generates image data based on the electrical signals output from the X-ray detector 22. In this manner, the X-ray tube 21 and the X-ray detector 22 capture the images of the subject.

Furthermore, the X-ray diagnostic device 1 also displays X-ray images based on the generated image data on the display device 2 or the like. When a desired site of the subject is not displayed on the display device 2, the operator moves the couchtop 11 in the horizontal direction manually or electrically. This allows the operator to include the desired site of the subject in the X-ray irradiation range, that is, in the display range of the image data. Note here that human-powered operation means that the operator moves the couchtop 11 manually by pushing it. Furthermore, motorized movement means that the couchtop 11 is moved by electric power.

Figure 2:
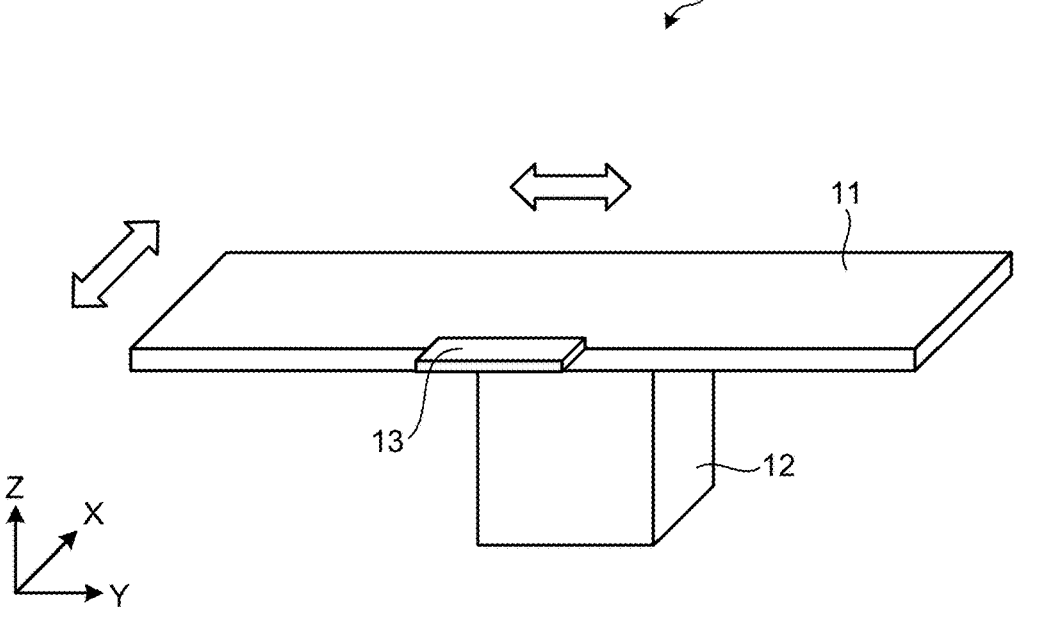
FIG. 2 is a perspective view illustrating an example of an appearance of a couch device according to the first embodiment.

Next, the appearance of the couch device 10 will be described. FIG. 2 is a perspective view illustrating an example of the appearance of the couch device 10 according to the first embodiment. The couch device 10 is a device that places the subject to a position for imaging by moving the subject as a scan target. The couch device 10 includes a base 12, the couchtop 11, and a console (control panel) 13. The base 12 is a casing that supports the couchtop 11.

The couchtop 11 is a plate on which the subject is placed and which can be moved in the horizontal direction. In more detail, the couchtop 11 is configured to be capable of being moved in the longitudinal direction of the couchtop 11, that is, in the Y-axis direction. The couchtop 11 is also configured to be capable of being moved in the direction (lateral direction) that is orthogonal to the longitudinal direction of the couchtop 11, that is, in the X-axis direction. Note that the couchtop 11 may also be provided on the top face of a support frame that supports the couchtop 11. When the couchtop 11 is supported by the support frame, the couchtop 11 may move along with the support frame or may move separately from the support frame.

The couchtop 11 includes, on its side face, the console 13 that accepts operations to move the couchtop 11. The console 13 accepts, for example, an instruction operation from the operator regarding movement of the couchtop 11 as an operation to move the couchtop 11. The console 13 includes buttons that accept various operations, a control lever (knob 13a and shaft 13b) and pressure-sensitive sensors 13c (see FIG. 7) to be described later. Note that the console 13 may include a miniature joystick 13d (see FIG. 10) instead of the pressure-sensitive sensor 13c. The console 13 is an example of an operation unit and an example of the input interface.

Figure 3:
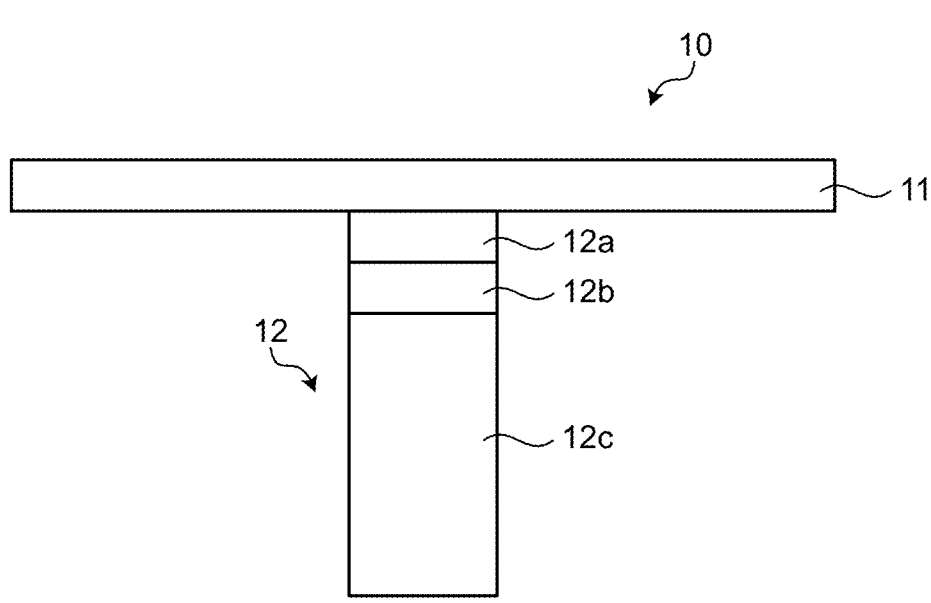
FIG. 3 is a diagram illustrating an example of a configuration of a base of the couch device according to the first embodiment.

FIG. 3 is a diagram illustrating an example of the configuration of the base 12 of the couch device 10 according to the first embodiment. As illustrated in FIG. 3, the base 12 includes a couchtop longitudinal mechanism 12a, a couchtop lateral mechanism 12b, and a couch up-and-down motion mechanism 12c. The couchtop longitudinal mechanism 12a, the couchtop lateral mechanism 12b, and the couch up-and-down motion mechanism 12c are examples of the drive mechanism.

The couchtop longitudinal mechanism 12a generates a driving force for moving the couchtop 11 in the longitudinal direction of the couchtop 11, and uses the generated driving force to move the couchtop 11 in the longitudinal direction of the couchtop 11. The couchtop longitudinal mechanism 12a includes, for example, a motor, an actuator, and the like, and a driving force is generated by the motor, the actuator, and the like. Furthermore, the couchtop longitudinal mechanism 12a has a conveyance mechanism with various components such as a gear, a conveyor belt, and a clutch, and transmits the driving force for moving the couchtop 11 to the conveyance mechanism. In other words, the couchtop longitudinal mechanism 12a moves the couchtop 11 by transmitting the driving force to the couchtop 11 via the conveyance mechanism. Referring to an example, the conveyance mechanism moves the couchtop 11 by rotating the gear and the conveyor belt in a state where the clutch is being connected. In this manner, the couchtop longitudinal mechanism 12a moves the couchtop 11 in the horizontal direction using the conveyance mechanism.

The couchtop lateral mechanism 12b generates a driving force for moving the couchtop 11 in the lateral direction of the couchtop 11, and uses the generated driving force to move the couchtop 11 in the lateral direction of the couchtop 11. Like the couchtop longitudinal mechanism 12a, the couchtop lateral mechanism 12b includes, for example, a motor, an actuator, and the like, and a driving force is generated by the motor, the actuator, and the like. Furthermore, like the couchtop longitudinal mechanism 12a, the couchtop lateral mechanism 12b has a conveyance mechanism with various components such as a gear, a conveyor belt, and a clutch, and transmits the driving force for moving the couchtop 11 to the conveyance mechanism. In other words, the couchtop lateral mechanism 12b moves the couchtop 11 by transmitting the driving force to the couchtop 11 via the conveyance mechanism. In this manner, the couchtop lateral mechanism 12b moves the couchtop 11 in the horizontal direction using the conveyance mechanism.

The couch up-and-down motion mechanism 12c generates a driving force for moving the couchtop 11 in the up-and-down direction of the couchtop 11, and uses the generated driving force to move the couchtop 11 in the up-and-down direction of the couchtop 11. Note that the up-and-down direction of the couchtop 11 is, for example, the vertical direction (Z-axis direction orthogonal to the X-axis direction and Y-axis direction described above). Like the couchtop longitudinal mechanism 12a, the couch up-and-down motion mechanism 12c includes, for example, a motor, an actuator, and the like, and a driving force is generated by the motor, the actuator, and the like. Furthermore, like the couchtop longitudinal mechanism 12*a*, the couch up-and-down motion mechanism 12*c* has a conveyance mechanism with various components such as a gear, a conveyor belt, and a clutch, and transmits the driving force for moving the couchtop 11 to the conveyance mechanism. In other words, the couch up-and-down motion mechanism 12*c* moves the couchtop 11 in the up-and-down direction by transmitting the driving force to the couchtop 11 via the conveyance mechanism.

Figure 4:
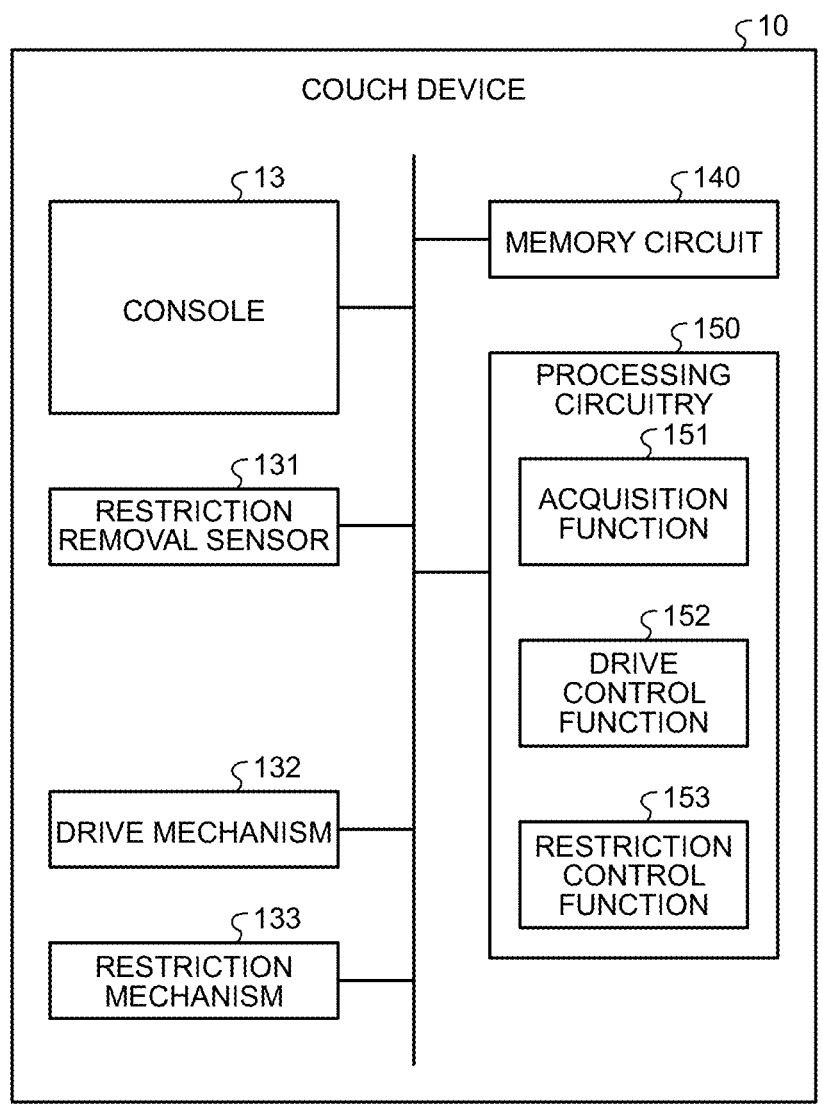
FIG. 4 is a diagram illustrating an example of the configuration of the couch device according to the first embodiment.

FIG. 4 is a diagram illustrating an example of the configuration of the couch device 10 according to the first embodiment. As illustrated in FIG. 4, the couch device 10 includes the console 13, a restriction removal sensor 131, a drive mechanism 132, a restriction mechanism 133, a memory circuit 140, and processing circuitry 150.

The restriction removal sensor 131 is a sensor for detecting that the control lever is pressed by the operator. For example, the restriction removal sensor 131 is implemented by a pressure-sensitive sensor. Upon detecting that the control lever is pressed by the operator, the restriction removal sensor 131 outputs an electrical signal to the processing circuitry 150 indicating that the control lever is pressed. Furthermore, upon detecting that the control lever is not pressed by the operator, the restriction removal sensor 131 outputs an electrical signal to the processing circuitry 150 indicating that the control lever is not pressed.

The drive mechanism 132 is a mechanism that includes the couchtop longitudinal mechanism 12*a*, the couchtop lateral mechanism 12*b*, and the couch up-and-down motion mechanism 12*c*.

The restriction mechanism 133 restricts the movement of the couchtop 11. For example, the restriction mechanism 133 has an electromagnetic lock or the like. The restriction mechanism 133 restricts the movement of the couchtop 11 by stopping the rotation and the like of the gear and the conveyor belt of the conveyance mechanism by the electromagnetic lock in a state where the clutch is being engaged. On the other hand, the restriction mechanism 133 removes the restriction on the movement of the couchtop 11 by releasing the conveyance mechanism stopped by the electromagnetic lock. Note here that the gear and the conveyor belt of the conveyance mechanism rotate when the operator or the like moves the couchtop 11 by human-powered operation. Therefore, the restriction mechanism 133 restricts not only the movement of the couchtop 11 by the driving force generated by the drive mechanism 132, but also the movement of the couchtop 11 by human-powered operation. The electromagnetic lock of the restriction mechanism 133 may restrict the movement of the couchtop 11 not only by stopping the conveyance mechanism, but also by pressing a component or hooking a component against other parts. Furthermore, the restriction mechanism 133 is not limited to using the electromagnetic lock, but may also use other mechanisms to restrict the movement of the couchtop 11.

The memory circuit 140 is a semiconductor memory element such as a random-access memory (RAN) or a flash memory, or a storage device such as a hard disk or an optical disc, and the like.

The processing circuitry 150 performs overall control of the couch device 10. For example, the processing circuitry 150 executes an acquisition function 151, a drive control function 152, and a restriction control function 153, as illustrated in FIG. 4. Here, for example, each of the processing functions executed by the acquisition function 151, the drive control function 152, and the restriction control function 153 that are structural components of the processing circuitry 150 illustrated in FIG. 4 is recorded in the memory circuit 140 in the form of a program that can be executed by a computer. The processing circuitry 150 is a processor that reads out each program from the memory circuit 140 and executes the program to implement the function corresponding to each program. In other words, the processing circuitry 150 after reading out each program comes to have each of the functions indicated within the processing circuitry 150 illustrated in FIG. 4.

Note that the term "processor" means, for example, a central processing unit (CPU), a graphics processing unit (GPU), or a circuit such as an application specific integrated circuit (ASIC) or a programmable logic device (for example, a simple programmable logic device (SPLD), a complex programmable logic device (CPLD), or a field programmable gate array (FPGA)). The processor implements the functions by reading out and executing the programs saved in the memory circuit 140. Instead of saving the programs in the memory circuit 140, the programs can be directly incorporated in the circuit of the processor. In this case, the processor implements the functions by reading out and executing the programs incorporated in the circuit. Note that each of the processors of the present embodiment is not limited to being configured as a single circuit for each processor, but may also be configured as a single processor by combining a plurality of independent circuits to implement the functions.

The acquisition function 151 acquires one of the weight applied to the couchtop 11 and the deflection amount of the couchtop 11. First, the case where the acquisition function 151 acquires the weight applied to the couchtop 11 will be described. For example, a load sensor for detecting the weight applied to the couchtop 11 is provided inside the couch device 10, and the acquisition function 151 acquires the weight applied to the couchtop 11 detected by the load sensor. Note that the acquisition function 151 may acquire the weight of the subject contained in examination information (examination data) regarding the subject to be the scan target as the weight applied to the couchtop 11. The acquisition function 151 is an example of the acquisition unit.

Next, the case where the acquisition function 151 acquires the deflection amount of the couchtop 11 will be described. For example, the acquisition function 151 acquires the weight applied to the couchtop 11 by the same method as the method described above, and calculates the deflection amount of the couchtop 11 from the acquired weight applied to the couchtop 11 and the current position of the couchtop 11 in the longitudinal direction. In this manner, the acquisition function 151 calculates the deflection amount of the couchtop 11 to acquire the deflection amount of the couchtop 11.

The drive control function 152 controls the drive mechanism 132 based on the operations accepted by the console 13. For example, the drive control function 152 controls the drive mechanism 132 to move the couchtop 11 in the direction in which the control lever (knob 13*a* and shaft 13*b*) of the console 13 is moved in parallel or in the direction in which it is tilted. Furthermore, the drive control function 152 has the drive mechanism 132 generate a driving force to move the couchtop 11 at a speed based on the operation amount of the operation indicating the moving direction of the couchtop 11 accepted by the control lever. For example, the drive control function 152 has the drive mechanism 132 generate a driving force to move the couchtop 11 at a speed corresponding to the moving amount of the control lever moved in parallel or to the tilted angle of the control lever. The drive control function 152 is an example of the control unit.

The restriction control function 153 controls the restriction mechanism 133 based on the operations accepted by the console 13. Furthermore, the restriction control function 153 controls the restriction mechanism 133 based on the electrical signals output from the restriction removal sensor 131. For example, the restriction control function 153 controls the restriction mechanism 133 to remove the restriction on the movement of the couchtop 11, when it is detected by the restriction removal sensor 131 that the control lever is pressed. Furthermore, the restriction control function 153 controls the restriction mechanism 133 to restrict the movement of the couchtop 11, when it is not detected by the restriction removal sensor 131 that the control lever is pressed.

The restriction control function 153 may also control the restriction mechanism 133 to remove the restriction on the movement of the couchtop 11 not only when it is detected by the restriction removal sensor 131 that the control lever is pressed but also based on other factors.

For example, the console 13 may include a restriction removal switch (restriction removal button) to remove the restriction on the movement of the couchtop 11. In this case, the console 13 accepts a removal instruction to remove the restriction on the movement of the couchtop 11 by the restriction mechanism 133, when the restriction removal button is pressed by the operator. The restriction control function 153 controls the restriction mechanism 133 to remove the restriction on the movement of the couchtop 11, when the removal instruction is accepted by the console 13. Therefore, the restriction on the movement of the couchtop 11 is not removed simply by pressing the control lever. Furthermore, the restriction control function 153 controls the restriction mechanism 133 to restrict the movement of the couchtop 11, when the restriction removal button is pushed in again. As described, the restriction control function 153 removes the restriction on the motorized movement upon accepting an operation indicating removal of the restriction on the motorized movement of the couchtop 11, thereby making it possible to prevent unintentional motorized movement of the couchtop 11 when the operator unexpectedly touches the control lever.

Furthermore, for example, a tactile sensor for removing the restriction on the movement of the couchtop 11 may be attached to the knob 13a to be described later. The tactile sensor detects that the knob 13a is gripped by the operator. In this case, the restriction control function 153 controls the restriction mechanism 133 to remove the restriction on the movement of the couchtop 11, when it is detected by the tactile sensor that the knob 13a is gripped by the operator. Furthermore, the restriction control function 153 controls the restriction mechanism 133 to restrict the movement of the couchtop 11, when it is not detected by the tactile sensor that the knob 13a is gripped by the operator.

Note that the configuration of the couch device 10 is not limited to the configuration described above by referring to FIG. 3 and FIG. 4. For example, the couch device 10 may have a tilt mechanism that tilts the couchtop 11. Thus, an example of the couch device 10 with a tilt mechanism will be described by referring to FIG. 5 and FIG. 6. In the following description, same reference signs are applied to the same structural components as those described above by referring to FIG. 3 and FIG. 4, and explanations thereof may be omitted.

Figure 5:
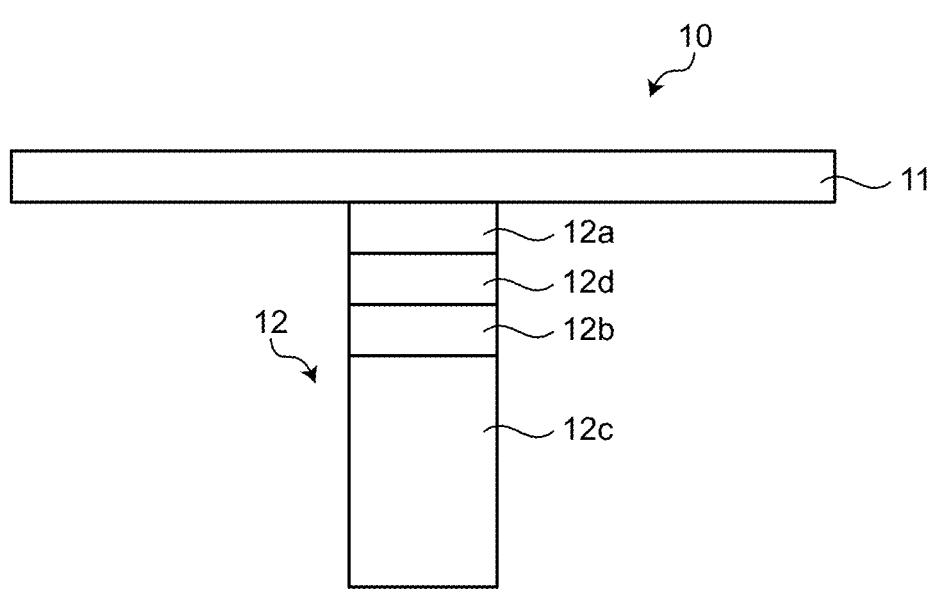
FIG. 5 is a diagram illustrating another example of the configuration of the base of the couch device according to the first embodiment.

FIG. 5 is a diagram illustrating another example of the configuration of the base 12 of the couch device 10 according to the first embodiment. As illustrated in FIG. 5, the base 12 includes a longitudinal tilt mechanism 12d in addition to the couchtop longitudinal mechanism 12a, the couchtop lateral mechanism 12b, and the couch up-and-down motion mechanism 12c. The longitudinal tilt mechanism 12d is an example of the drive mechanism.

The longitudinal tilt mechanism 12d generates a driving force for tilting the couchtop 11, and uses the generated driving force to tilt the couchtop 11. For example, the longitudinal tilt mechanism 12d tilts the couchtop 11 by rotating the couchtop 11 around an axis parallel to the lateral direction (X-axis direction) of the couchtop 11. The longitudinal tilt mechanism 12d includes, for example, a motor, an actuator, and the like, and a driving force is generated by the motor, the actuator, and the like. The longitudinal tilt mechanism 12d has a conveyance mechanism with various components such as a gear, a conveyor belt, and a clutch, and transmits the driving force for tilting the couchtop 11 to the conveyance mechanism. In other words, the longitudinal tilt mechanism 12d tilts the couchtop 11 by transmitting the driving force to the couchtop 11 via the conveyance mechanism. Referring to an example, the conveyance mechanism tilts the couchtop 11 by rotating the gear and the conveyor belt in a state where the clutch is being engaged.

Figure 6:
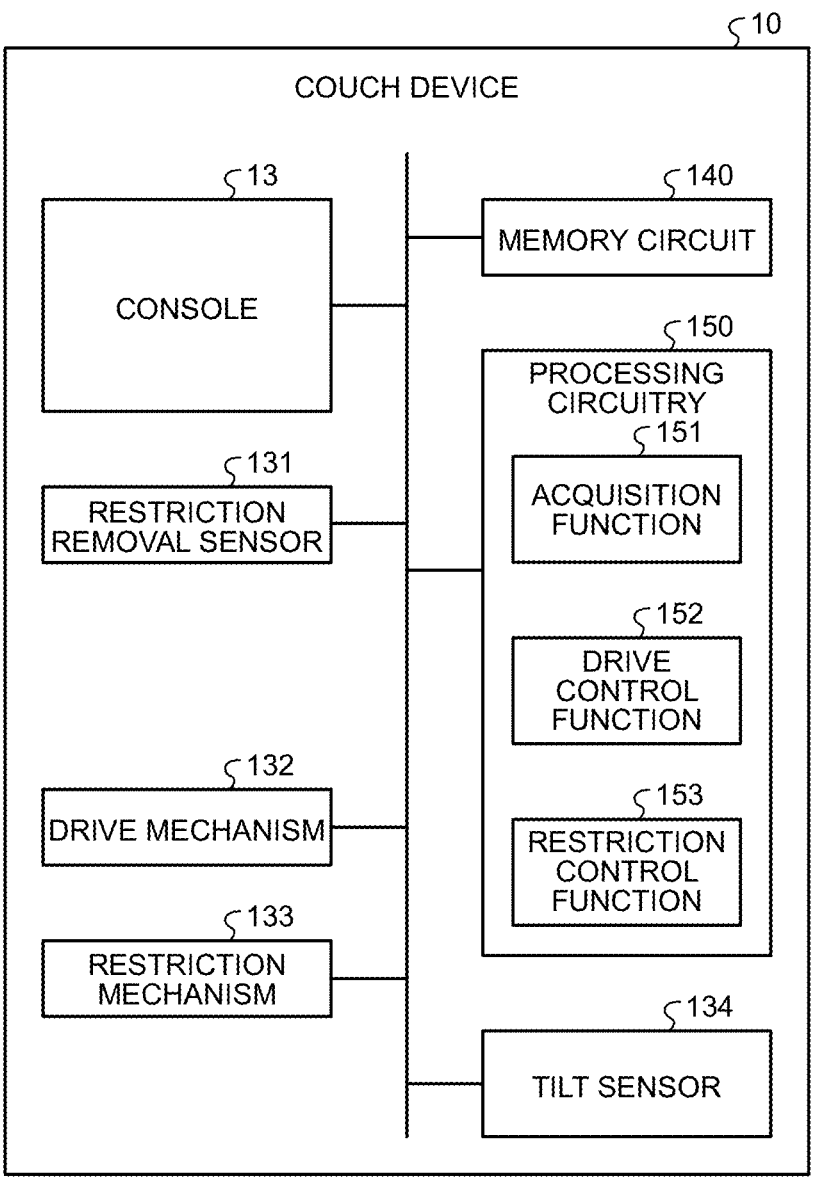
FIG. 6 is a diagram illustrating another example of the configuration of the couch device according to the first embodiment.

FIG. 6 is a diagram illustrating another example of the configuration of the couch device 10 according to the first embodiment. The couch device 10 illustrated in FIG. 6 includes a tilt sensor 134 in addition to the configuration of the couch device 10 illustrated in FIG. 4 mentioned earlier.

The tilt sensor 134 is a sensor that detects the tilt angle of the couchtop 11. For example, the tilt sensor 134 detects the tilt angle of the couchtop 11 with respect to the horizontal direction. The tilt sensor 134 then outputs an electrical signal indicating the detected tilt angle to the processing circuitry 150. The tilt angle herein is, for example, the rotation angle of the couchtop 11 around the axis of rotation. Therefore, in a state where the longitudinal direction of the couchtop 11 coincides with the horizontal direction, the tilt sensor 134 detects 0 degrees as the tilt angle of the couchtop 11.

Figure 7:
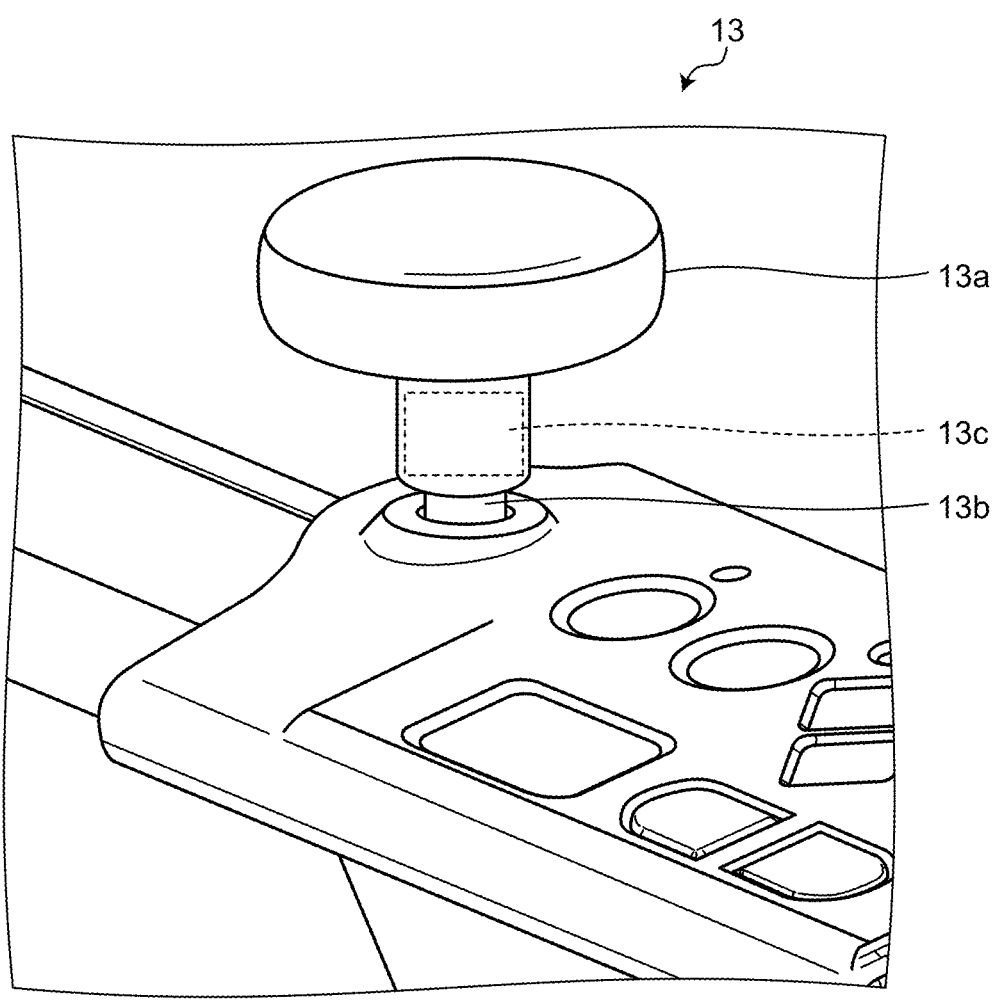
FIG. 7 is a diagram illustrating an example of a configuration of a console according to the first embodiment.
Figure 8:
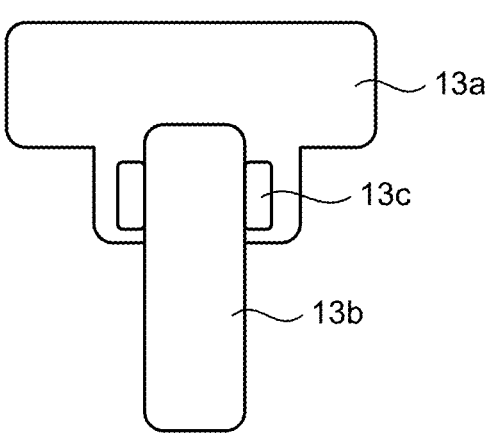
FIG. 8 is a cross-sectional view of a control lever according to the first embodiment.
Figure 9:
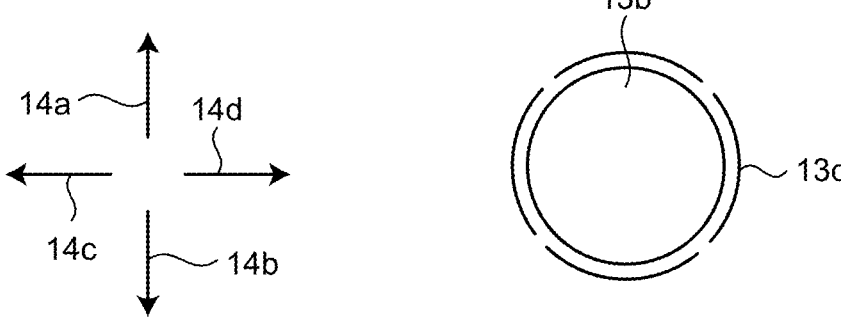
FIG. 9 is a diagram illustrating an example of an arrangement relationship of the components configuring the control lever when the control lever according to the first embodiment is viewed from above.

Next, an example of the configuration of the console 13 will be described. FIG. 7 is a diagram illustrating an example of the configuration of the console 13 according to the first embodiment. FIG. 7 illustrates an example of the control lever provided to the console 13. The control lever accepts the above-described instruction operations given by the operator. FIG. 8 is a cross-sectional view of the control lever according to the first embodiment. FIG. 8 illustrates a cross-sectional view of the control lever cut in a prescribed cutting plane (for example, Y-Z plane). FIG. 9 is a diagram illustrating an example of an arrangement relationship of the components configuring the control lever when the control lever according to the first embodiment is viewed from above. As illustrated in FIGS. 7 to 9, the console 13 includes the control lever and the pressure-sensitive sensor 13c, and the control lever includes the knob 13a and the shaft 13b.

In the present embodiment, when moving the couchtop 11 manually, the operator moves the control lever in parallel to the horizontal direction to move the couchtop 11 horizontally in conjunction with the parallel movement of the control lever.

The knob 13a is a member that is held by the operator, when the operator manually moves the couchtop 11. The knob 13a is provided at one end of the shaft 13b and connected to the shaft 13b.

The shaft 13b is a rod-shaped member, and it is supported by the casing in a manner capable of being pushed into the casing of the console 13 and also supported by the casing in a manner capable of being moved in parallel.

The pressure-sensitive sensor 13c is disposed around the shaft 13b. For example, the pressure-sensitive sensor 13c is disposed to surround the outer periphery of the shaft 13b. When the control lever is not moved in parallel by the operator, there is a gap formed between the pressure-sensitive sensor 13c and the shaft 13b. In other words, there is so-called "play" between the pressure-sensitive sensor 13c and the shaft 13b. In the present embodiment, as illustrated in FIG. 9, each of the four pressure-sensitive sensors 13c is provided to correspond to each of the four directions indicated by arrows 14a to 14d. For example, the direction indicated by the arrow 14a is the direction to the left side of the subject, and the direction indicated by the arrow 14b is the direction to the right side of the subject. The directions indicated by the arrows 14a and 14b correspond to the lateral direction of the couchtop 11. The direction indicated by the arrow 14c is the direction to the head side of the subject, and the direction indicated by the arrow 14d is the direction to the foot side of the subject. The directions indicated by the arrows 14c and 14d correspond to the longitudinal direction of the couchtop 11.

For example, when moving the couchtop 11 in the direction to the left side of the subject, the operator moves the control lever in parallel to the direction indicated by the arrow 14a. In this case, a force is applied by the shaft 13b of the control lever to the pressure-sensitive sensor 13c that is provided to correspond to the direction indicated by the arrow 14a. Then, the pressure-sensitive sensor 13c that is provided to correspond to the direction indicated by the arrow 14a detects the magnitude of the force applied by the shaft 13b of the control lever, and outputs an electrical signal indicating the magnitude of the detected force to the processing circuitry 150. In this manner, the drive control function 152 of the processing circuitry 150 acquires, from the pressure-sensitive sensor 13c, an electrical signal indicating the magnitude of the force that is applied to the couchtop 11 when the couchtop 11 is moved by the operator. The drive control function 152 then acquires the magnitude of the force indicated by the electrical signal as the magnitude of the force applied to the couchtop 11. The drive control function 152 also acquires the operation amount of the control lever from the magnitude of the force applied to the couchtop 11. The operations described above are the same for the other directions as well.

Furthermore, the drive control function 152 determines from which of the pressure-sensitive sensors 13c provided to correspond to the four directions indicated by the arrows 14a to 14d the acquired electrical signal is output. Then, based on the determination result, the drive control function 152 determines that the acquired electrical signal is the signal indicating the magnitude of the force applied in which direction to the couchtop 11. For example, a case will be described in which the drive control function 152 determines that the acquired electrical signal is the electrical signal output from the pressure-sensitive sensor 13c that is provided to correspond to the direction indicated by the arrow 14a. In this case, the drive control function 152 determines that the acquired electrical signal is the signal indicating the magnitude of the force applied to the couchtop 11 in the direction to the left side of the subject. The drive control function 152 then acquires the moving direction of the couchtop 11 manually by the operator based on the determination result. For example, when determined that the acquired electrical signal is the signal indicating the magnitude of the force applied to the couchtop 11 in the direction to the left side of the subject, the drive control function 152 acquires the direction to the left side of the subject as the moving direction of the couchtop 11. The drive control function 152 executes the same processing for the other directions as well. As described above, the pressure-sensitive sensor 13c and the drive control function 152 detect, as the instruction operation, at least one of the moving direction of the shaft 13b and the magnitude of the force applied to the shaft 13b by the operation of the operator. The pressure-sensitive sensor 13c is an example of a detection unit and an example of a detection mechanism. The drive control function 152 is also an example of the detection unit.

Note that the configuration of the control lever is not limited to the configuration described above by referring to FIGS. 7 to 9. For example, the control lever may include a miniature joystick instead of the pressure-sensitive sensor 13c. Therefore, an example of the configuration of the control lever equipped with a miniature joystick will be described by referring to FIG. 10 and FIG. 11. In the following description, same reference signs are applied to the same structural components as those described above by referring to FIGS. 7 to 9, and explanations thereof may be omitted.

Figure 10:
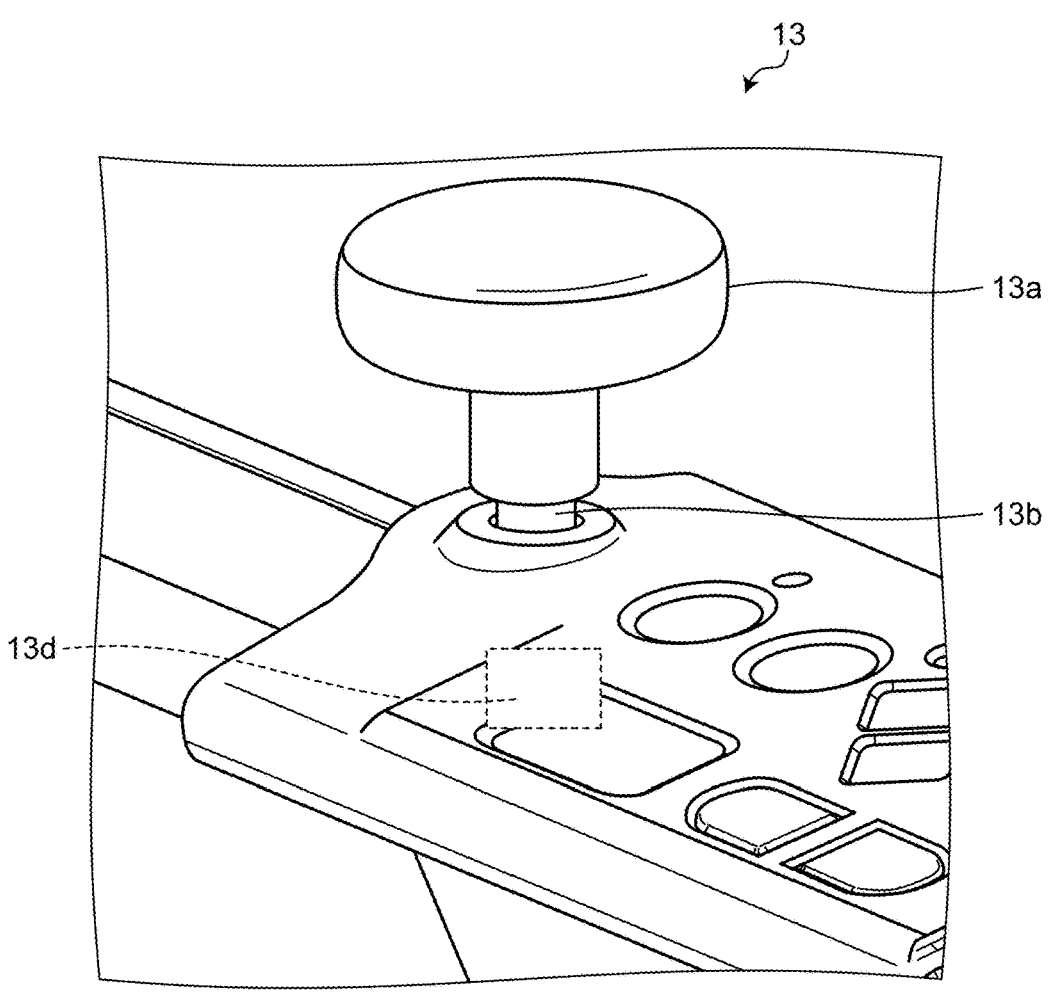
FIG. 10 is a diagram illustrating another example of the configuration of the control lever according to the first embodiment.
Figure 11:
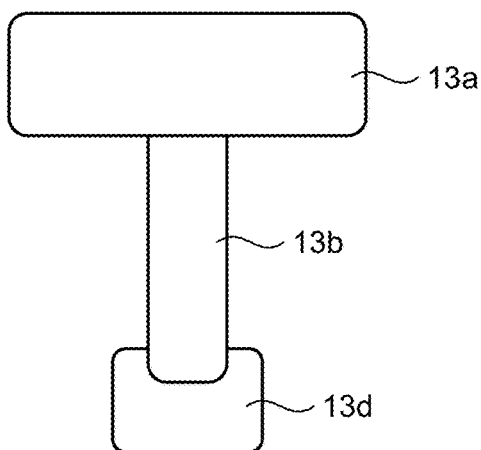
FIG. 11 is a cross-sectional view of the control lever illustrated in FIG. 10.

FIG. 10 is a diagram illustrating another example of the configuration of the control lever according to the first embodiment. FIG. 11 is a cross-sectional view of the control lever illustrated in FIG. 10. FIG. 11 illustrates a cross-sectional view of the control lever cut in a prescribed cutting plane (for example, Y-Z plane). As illustrated in FIGS. 10 and 11, the console 13 includes the miniature joystick 13d.

As illustrated in FIG. 11, the knob 13a is provided at one end of the shaft 13b, and the miniature joystick 13d is provided at the other end of the shaft 13b. The control lever is supported by the miniature joystick 13d such that it can be tilted by the operator against the miniature joystick 13d. The operator moves the couchtop 11 in the horizontal direction by moving the control lever in parallel in a state where the control lever is being tilted to the direction in which the couchtop 11 is desired to be moved. The miniature joystick 13d detects the direction in and angle at which the control lever is tilted. The miniature joystick 13d then outputs an electrical signal indicating the detected direction and angle to the processing circuitry 150. In this manner, the drive control function 152 of the processing circuitry 150 acquires, from the miniature joystick 13d, the electrical signal indicating the direction in and angle at which the control lever is tilted. The drive control function 152 then acquires the direction indicated by the electrical signal as the moving direction of the couchtop 11. The drive control function 152 also acquires the operation amount of the control lever and the magnitude of the force applied to the couchtop 11 from the angle indicated by the electrical signal. As described above, the miniature joystick 13d and the drive control function 152 detect, as the instruction operation, at least one of the moving direction of the shaft 13b and the magnitude of the force applied to the shaft 13b by the operation of the operator. The miniature joystick 13d is an example of the detection unit and an example of the detection mechanism. In the case illustrated in FIGS. 10 and 11, each of the four pressure-sensitive sensors 13c, instead of the miniature joystick 13d, may be provided at the other end of the shaft 13b to correspond to each of the four directions indicated by the arrows 14a to 14d (see FIG. 9). Then, the same processing may be performed using the four pressure-sensitive sensors 13c.

As described above, the console 13 includes the pressure-sensitive sensors 13c or the miniature joystick 13d for detecting at least one of the moving direction of the couchtop 11 and the moving amount of the couchtop 11 moved in the moving direction. Then, the console 13 accepts at least one of the moving direction of the couchtop 11 detected by the pressure-sensitive sensor 13c or the miniature joystick 13d and the moving amount of the couchtop 11 moved in the moving direction as the instruction operation regarding movement of the couchtop 11. The pressure-sensitive sensor 13c and the miniature joystick 13d are examples of the detection unit and examples of the detection mechanism.

Figure 12:
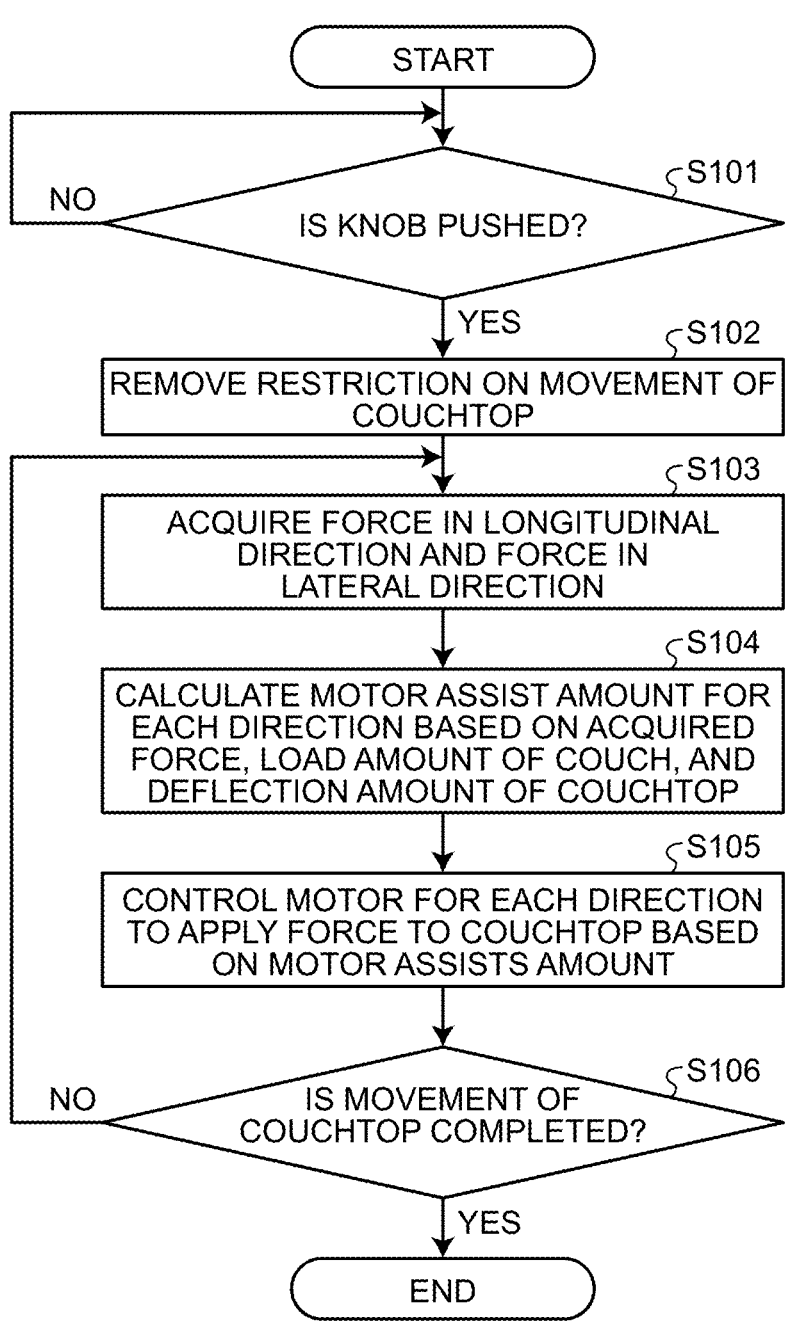
FIG. 12 is a flowchart indicating an example of a flow of processing executed by the couch device when assisting manual movement of the couchtop in the first embodiment.

In the present embodiment, the couch device 10 assists manual movement of the couchtop 11 when the operator moves the couchtop 11 manually. FIG. 12 is a flowchart indicating an example of a flow of processing executed by the couch device 10 when assisting manual movement of the couchtop 11 in the first embodiment. In a case where the couch device 10 includes the longitudinal tilt mechanism 12d, the processing indicated in FIG. 12 is executed when the tilt angle of the couchtop 11 indicated by the electrical signal output from the tilt sensor 134 is 0 degrees, that is, when the longitudinal direction of the couchtop 11 coincides with the horizontal direction.

As illustrated in FIG. 12, the drive control function 152 determines whether the knob 13a (control lever) is pushed in based on the electrical signal output from the restriction removal sensor 131 (step S101). When the knob 13a is not pushed in (No at step S101), the drive control function 152 again makes the determination at step S101.

On the other hand, when the knob 13a is pushed in (Yes at step S101), the restriction control function 153 controls the restriction mechanism 133 to remove the restriction on the movement of the couchtop 11 (step S102).

Then, the drive control function 152 acquires the magnitude of the force applied to the couchtop 11 in the longitudinal direction of the couchtop 11 and the magnitude of the force applied to the couchtop 11 in the lateral direction of the couchtop 11 from the electrical signal output from the pressure-sensitive sensor 13c or the miniature joystick 13d (step S103). In other words, the magnitude of the force acquired at step S103 is the magnitude of the force applied to the couchtop 11 manually by the operator.

The drive control function 152 then calculates the motor assist amount for each of the longitudinal direction and the lateral direction of the couchtop 11 from the magnitude of the force applied to the couchtop 11 manually by the operator and one of the weight applied to the couchtop 11 and the deflection amount of the couchtop 11 acquired by the acquisition function 151 (step S104). Note here that the motor assist amount is, for example, for reducing the load when the operator manually moves the couchtop 11, and it is the magnitude of the force applied by the motor to the couchtop 11 in the direction in which the operator moves the couchtop 11.

Figure 13:
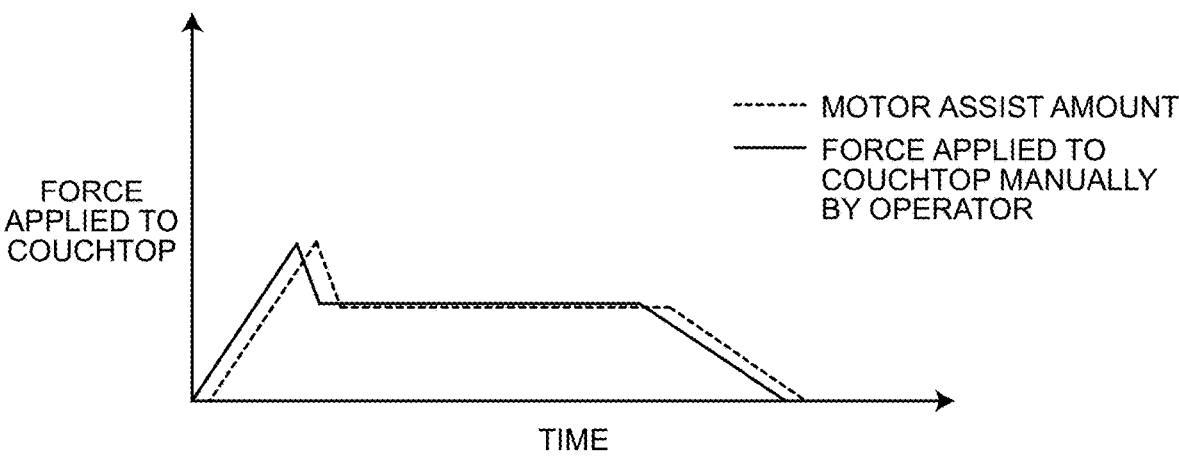
FIG. 13 is a graph indicating the relationship between the magnitude of the force acquired at step S103 and the motor assist amount calculated at step S104 in either direction in the first embodiment.

FIG. 13 is a graph indicating the relationship between the magnitude of the force acquired at step S103 and the motor assist amount calculated at step S104 in either direction in the first embodiment. In the graph illustrated in FIG. 13, the horizontal axis represents time, and the vertical axis represents the magnitude of the force applied to the couchtop 11. In FIG. 13, the solid line indicates the magnitude of the force acquired at step S103, that is, the magnitude of the force applied to the couchtop 11 manually by the operator. The dashed line indicates the motor assist amount. In the example in FIG. 13, the drive control function 152 calculates the motor assist amount same as the magnitude of the force applied to the couchtop 11 manually by the operator, although there is a time lag. Note that the drive control function 152 may calculate the motor assist amount such that the greater the weight applied to the couchtop 11, the greater the motor assist amount. The drive control function 152 may also calculate the motor assist amount such that the greater the deflection amount of the couchtop 11, the greater the motor assist amount.

As described above, the drive control function 152 determines the driving force to be generated by the drive mechanism 132 based on one of the weight applied to the couchtop 11 and the deflection amount of the couchtop 11 and on the instruction operation described above.

Then, the drive control function 152 controls the motor of the drive mechanism 132 such that a force based on the motor assist amount is applied to the couchtop 11 for each of the longitudinal direction and the lateral direction of the couchtop 11 (step S105). Thereby, the force based on the motor assist amount is applied to the couchtop 11 for each of the directions. As described, since a force based on an appropriate motor assist amount considering the weight applied to the couchtop 11 or the deflection amount of the couchtop 11 is applied to the couchtop 11, the load of the operator who moves the couchtop 11 manually can be reduced appropriately. Furthermore, since the operator moves the couchtop 11 manually, it is possible to perform fine positioning of the couchtop 11. Therefore, with the X-ray diagnostic device 1 and the couch device 10 according to the present embodiment, it is possible to perform fine positioning while reducing the load of the operator when the operator moves the couchtop 11. As described, with the X-ray diagnostic device 1 and the couch device 10 according to the present embodiment, it is possible to improve the operability of the operations for moving the couchtop 11.

The drive control function 152 determines whether the movement of the couchtop 11 is completed based on the electrical signal output from the restriction removal sensor 131 (step S106). For example, the drive control function 152 determines that the movement of the couchtop 11 is completed when the electrical signal from the restriction removal sensor 131 indicates that the knob 13a is not pushed in. When determined that the movement of the couchtop 11 is completed (Yes at step S106), the drive control function 152 ends the processing indicated in FIG. 12.

On the other hand, the drive control function 152 determines that the movement of the couchtop 11 is not completed when the electrical signal from the restriction removal sensor 131 indicates that the knob 13a is pushed in. When determined that the movement of the couchtop 11 is not completed (No at step S106), the drive control function 152 returns to step S103.

When the pressure-sensitive sensor 13c or the miniature joystick 13d is malfunctioning, the couch device 10 cannot accurately acquire the magnitude of the force that is applied to the couchtop 11 manually by the operator. Therefore, the couch device 10 is unable to calculate the appropriate motor assist amount. In this case, a greater force is required when the operator tries to move the couchtop 11 manually without having the above-described assistance by the drive mechanism 132. Thus, when the pressure-sensitive sensor 13c or the miniature joystick 13d is malfunctioning, the drive control function 152 disconnects the motor from the couchtop 11 by disengaging the clutch of the conveyance mechanism of the drive mechanism 132. The drive control function 152 disconnects the motor from the couchtop 11, thereby allowing the operator to move the couchtop 11 with a relatively small force. Note that the drive control function 152 may determine that the pressure-sensitive sensor 13c or the miniature joystick 13d is malfunctioning based on the electrical signal output from the pressure-sensitive sensor 13c or the miniature joystick 13d. The drive control function 152 may also determine that the pressure-sensitive sensor 13c or the miniature joystick 13d is malfunctioning, when an emergency button provided to the console 13 is pressed by the operator.

Second Embodiment

Note that the drive control function 152 may change the algorithm used to calculate the motor assist amount (motor assist amount calculation algorithm) in response to an instruction from the operator. The X-ray diagnostic device 1 and the couch device 10 performing such processing will be described as the X-ray diagnostic device 1 and the couch device 10 according to the second embodiment. In the description of the second embodiment, the configurations that differ from those of the first embodiment will mainly be described and descriptions for the configurations similar to those of the first embodiment may be omitted.

Figure 14:
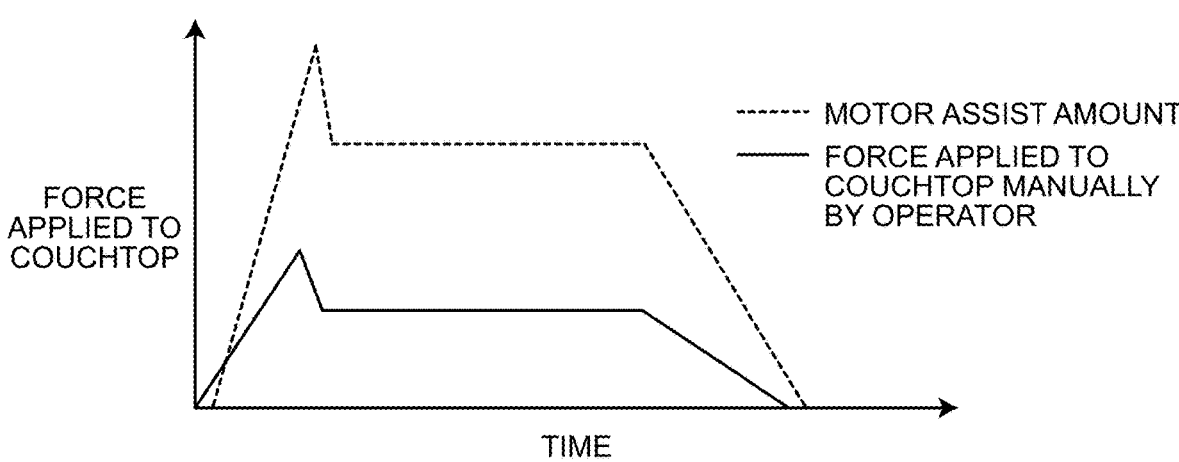
FIG. 14 is a graph indicating the relationship between the magnitude of the force acquired at step S103 and the motor assist amount calculated at step S104 in either direction in a second embodiment.

For example, a case will be described in which the operator inputs an instruction via the console 13 to change the motor assist amount calculation algorithm for calculating the motor assist amount from "motor assist amount calculation algorithm A" to "motor assist amount calculation algorithm B". It is assumed herein that the motor assist amount indicated in FIG. 13 mentioned earlier is calculated using "motor assist amount calculation algorithm A". In this case, the drive control function 152 calculates the motor assist amount indicated in FIG. 14 using "motor assist amount calculation algorithm B" at step S104. FIG. 14 is a graph indicating the relationship between the magnitude of the force acquired at step S103 and the motor assist amount calculated at step S104 in either direction in the second embodiment. In the graph illustrated in FIG. 14, the horizontal axis represents time, and the vertical axis represents the magnitude of the force applied to the couchtop 11. In FIG. 14, the solid line indicates the magnitude of the force acquired at step S103. The dashed line indicates the motor assist amount. In the example in FIG. 14, the drive control function 152 calculates the motor assist amount that is twice the magnitude of the force applied to the couchtop 11 manually by the operator, although there is a time lag. Thereby, the load of the operator can be reduced further in the case indicated in FIG. 14 compared to the case indicated in FIG. 13.

By switching the various switches such as dip switches or rotary switches provided on the internal substrate of the console 13, the drive control function 152 may switch the motor assist amount calculation algorithms used to calculate the motor assist amount.

Third Embodiment

The first embodiment is described by referring to the case where the couch device 10 includes the longitudinal tilt mechanism 12d, and executes the processing illustrated in FIG. 12 when the longitudinal direction of the couchtop 11 coincides with the horizontal direction. Note here that other processing may be executed when the couch device 10 includes the longitudinal tilt mechanism 12d and the tilt angle of the couchtop 11 indicated by the electrical signal output from the tilt sensor 134 is not 0 degrees, that is, when the longitudinal direction of the couchtop 11 is tilted with respect to the horizontal direction. Thus, the X-ray diagnostic device 1 and the couch device 10 executing other processing in this way will be described as the X-ray diagnostic device 1 and the couch device 10 according to the third embodiment. In the description of the third embodiment, the configurations that differ from those of the other embodiments will mainly be described and descriptions for the configurations similar to those of the other embodiments may be omitted.

Figures 15, 16:
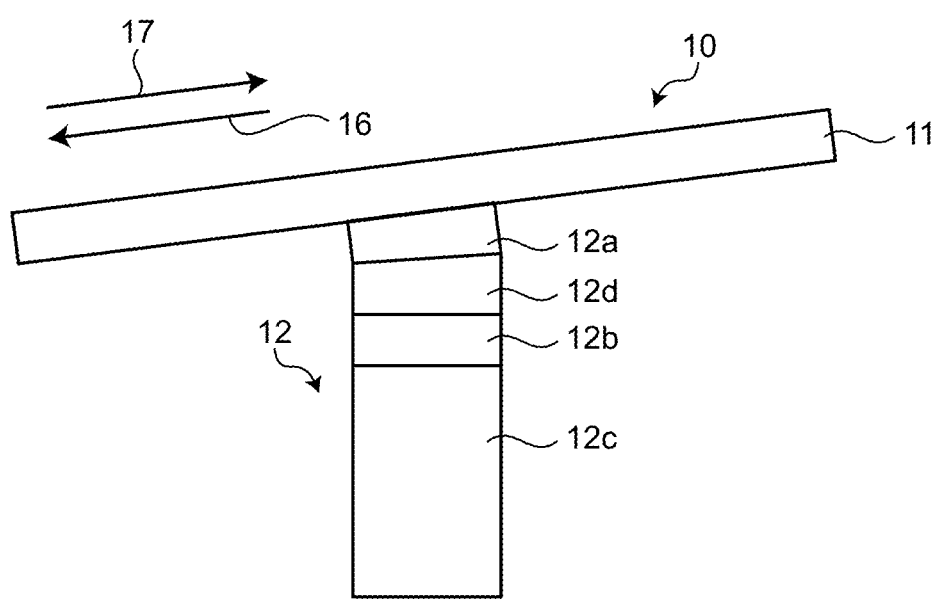
FIG. 15 is a diagram for describing an example of the processing executed by the couch device according to a third embodiment.
FIG. 16 is a diagram illustrating an example of a data structure of a table used in a fourth embodiment.

FIG. 15 is a diagram for describing an example of the processing executed by the couch device 10 according to the third embodiment. In the example in FIG. 15, the couchtop 11 is tilted. Therefore, when the operator tries to move the couchtop 11 manually in the direction indicated by an arrow 16, the force applied to the couchtop 11 may become too great since a component of the own weight of the couchtop 11 is originally applied to the couchtop 11 in the direction indicated by the arrow 16. In this case, it is difficult for the operator to perform fine positioning of the couchtop 11.

Therefore, at step S104, the drive control function 152 further calculates the motor assist amount by considering the force applied to the couchtop 11 in the opposite direction (the direction indicated by an arrow 17) to the direction indicated by the arrow 16 to offset the component of the own weight of the couchtop 11 applied to the couchtop 11 in the direction indicated by the arrow 16. For example, the drive control function 152 calculates the component of the own weight of the couchtop 11 applied to the couchtop 11 in the direction indicated by the arrow 16 based on the tilt angle and the tilt direction of the couchtop 11. Then, the drive control function 152 calculates the force applied to the couchtop 11 and the direction in which the force is applied to the couchtop 11 to offset the calculated component of the own weight. The drive control function 152 then calculates the motor assist amount by considering the force and the direction to offset the calculated component of the own weight. In this manner, in the third embodiment, the drive control function 152 calculates the motor assist amount based on the tilt angle and the tilt direction of the couchtop 11. This makes it possible to prevent the force applied to the couchtop 11 from becoming too great. As a result, the operator can perform fine positioning of the couchtop 11 even when the couchtop 11 is tilted.

Fourth Embodiment

The magnitude of the force that can be applied to the couchtop 11 varies depending on operators. Some operators can apply only a relatively small force to the couchtop 11, while others can apply a relatively large force to the couchtop 11. It is preferable to use a relatively large amount of motor assist to assist the operator who can apply only a relatively small force to the couchtop 11. In addition, the operator who can apply a relatively large force to the couchtop 11 can be assisted using a relatively small motor assist amount, resulting in assist with a smaller amount of power consumption. Therefore, it is preferable to calculate the motor assist amount corresponding to the operator. Thus, the X-ray diagnostic device 1 and the couch device 10 calculating the motor assist amount corresponding to the operator in this way will be described as the X-ray diagnostic device 1 and the couch device 10 according to the fourth embodiment. In the description of the fourth embodiment, the configurations that differ from those of the other embodiments will mainly be described and descriptions for the configurations similar to those of the other embodiments may be omitted.

FIG. 16 is a diagram illustrating an example of a data structure of a table 141 used in the fourth embodiment. The table 141 illustrated in FIG. 16 is stored in the memory circuit 140, and it is used when the couch device 10 calculates the motor assist amount.

In the table 141, a record in which an operator identification (ID) that is an identifier of an operator is associated with a motor assist amount calculation algorithm is registered for each operator indicated by the operator ID.

For example, in the table 141, the number of records corresponding to the number of operators are registered. One record has items of "operator ID" and "motor assist amount calculation algorithm". The operator ID is registered in the item "operator ID". The operator ID is an identifier for identifying the operator. In the item "motor assist amount calculation algorithm", a motor assist amount calculation algorithm for calculating the appropriate motor assist amount for the operator indicated by the operator ID is registered.

For example, in the first record of the table 141 illustrated in FIG. 16, "motor assist amount calculation algorithm A" for calculating a relatively small motor assist amount is registered for the operator ID "AA" that indicates an operator who can apply a relatively large force to the couchtop 11.

Furthermore, for example, in the second record of the table 141 illustrated in FIG. 16, "motor assist amount calculation algorithm B" for calculating a relatively large motor assist amount is registered for the operator ID "BB" that indicates an operator who can apply only a relatively small force to the couchtop 11.

In the fourth embodiment, the drive control function 152 acquires the operator ID at step S104. For example, the drive control function 152 may acquire the operator ID contained in the examination information (examination data). Furthermore, the drive control function 152 performs image analysis to specify the operator ID on the image data acquired by capturing images of the operator by a camera provided in an examination room where the X-ray diagnostic device 1 is disposed. The drive control function 152 may then acquire the operator ID that is acquired as a result of image analysis. Furthermore, the drive control function 152 refers to the table 141 to acquire the motor assist amount calculation algorithm corresponding to the acquired operator ID. The drive control function 152 then calculates the motor assist amount using the acquired motor assist amount calculation algorithm. In this manner, the drive control function 152 determines the driving force corresponding to the operator.

With the X-ray diagnostic device 1 and the couch device 10 according to the fourth embodiment, it is possible to calculate the appropriate motor assist amount for each operator by calculating the motor assist amount corresponding to the operator.

Fifth Embodiment

There may be a case where the operator, in a state where the X-ray diagnostic device 1 emits the X-rays to the subject and displays an X-ray fluoroscopic image on the display device 2, performs fine adjustment of the position of the couchtop 11 by checking the X-ray fluoroscopic image and gradually moving the couchtop 11 on which the subject is placed such that the site of interest is more appropriately displayed. In this case, it is preferable to assist the operator with a relatively small motor assist amount in order to allow the operator to perform fine adjustment of the position of the couchtop 11 with high precision. Note that the mode described above in which the X-rays are emitted to the subject and the X-ray fluoroscopic image to be checked by the operator is displayed on the display device 2 is also referred to as fluoroscopic mode.

Furthermore, in a case that is not the fluoroscopic mode, a case where the moving speed of the couchtop 11 is relatively fast, and the like, it is preferable to use a relatively large motor assist amount for assistance, since there is no need to perform fine adjustment of the position of the couchtop 11.

Therefore, it is preferable to calculate the motor assist amount corresponding to a status. Thus, the X-ray diagnostic device 1 and the couch device 10 calculating the motor assist amount corresponding to the status in this way will be described as the X-ray diagnostic device 1 and the couch device 10 according to the fifth embodiment. In the description of the fifth embodiment, the configurations that differ from those of the other embodiments will mainly be described and descriptions for the configurations similar to those of the other embodiments may be omitted.

Figure 17:
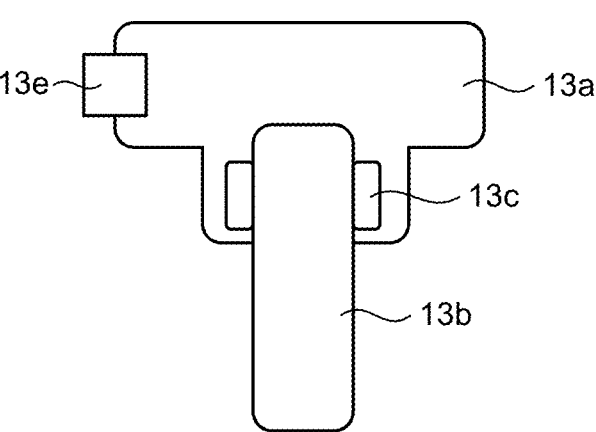
FIG. 17 is a cross-sectional view of an example of the control lever according to a fifth embodiment.

FIG. 17 is a cross-sectional view of an example of the control lever according to the fifth embodiment. FIG. 17 illustrates a cross-sectional view of the control lever cut in a prescribed cutting plane (for example, Y-Z plane). As illustrated in FIG. 17, the console 13 includes the control lever (knob 13*a* and shaft 13*b*), the pressure-sensitive sensor 13*c*, and a fine adjustment button (fine adjustment switch) 13*e*. Note here that the console 13 illustrated in FIG. 17 has the fine adjustment button 13*e* provided on the outer periphery of the knob 13*a* of the console 13 illustrated in FIG. 8. Note that the console 13 according to the fifth embodiment may be the one in which the fine adjustment button 13*e* is provided on the outer periphery of the knob 13*a* of the console 13 illustrated in FIG. 8. Furthermore, the fine adjustment button 13*e* may be provided on the inner side of the knob 13*a*.

The fine adjustment button 13*e* is connected to the processing circuitry 150, and it is implemented by a tactile switch (push switch). When performing fine adjustment of the position of the couchtop 11 in a status of the fluoroscopic mode or the like, the operator moves the couchtop 11 by operating the control lever while pressing the fine adjustment button 13*e*. The fine adjustment button 13*e* is provided on the knob 13*a* to be positioned in the vicinity of the thumb or index finger of a hand (right hand or left hand) of the operator while the operator is holding the knob 13*a*. This allows the operator to easily press the fine adjustment button 13*e*. Furthermore, for moving the couchtop 11 at a relatively high speed without fine adjustment of the position of the couchtop 11, the operator moves the couchtop 11 by operating the control lever without pressing the fine adjustment button 13*e*. Examples of the case where the operator desires to move the couchtop 11 at a relatively high speed may be a case where the couchtop 11 is returned to the initial position for allowing the operator to detach the various devices attached to the couchtop 11, a case where the couchtop 11 is returned to the initial position for allowing the subject to get on and off the couchtop 11, and cases of starting and stopping the movement of the couchtop 11.

The fine adjustment button 13*e* outputs a signal indicating ON to the processing circuitry 150 when pressed, and outputs a signal indicating OFF to the processing circuitry 150 when not pressed. Note that the fine adjustment button 13*e* may be implemented by a toggle switch instead of a tactile switch. The fine adjustment button 13*e* is an example of the operation unit and an example of the input interface.

Figure 18:
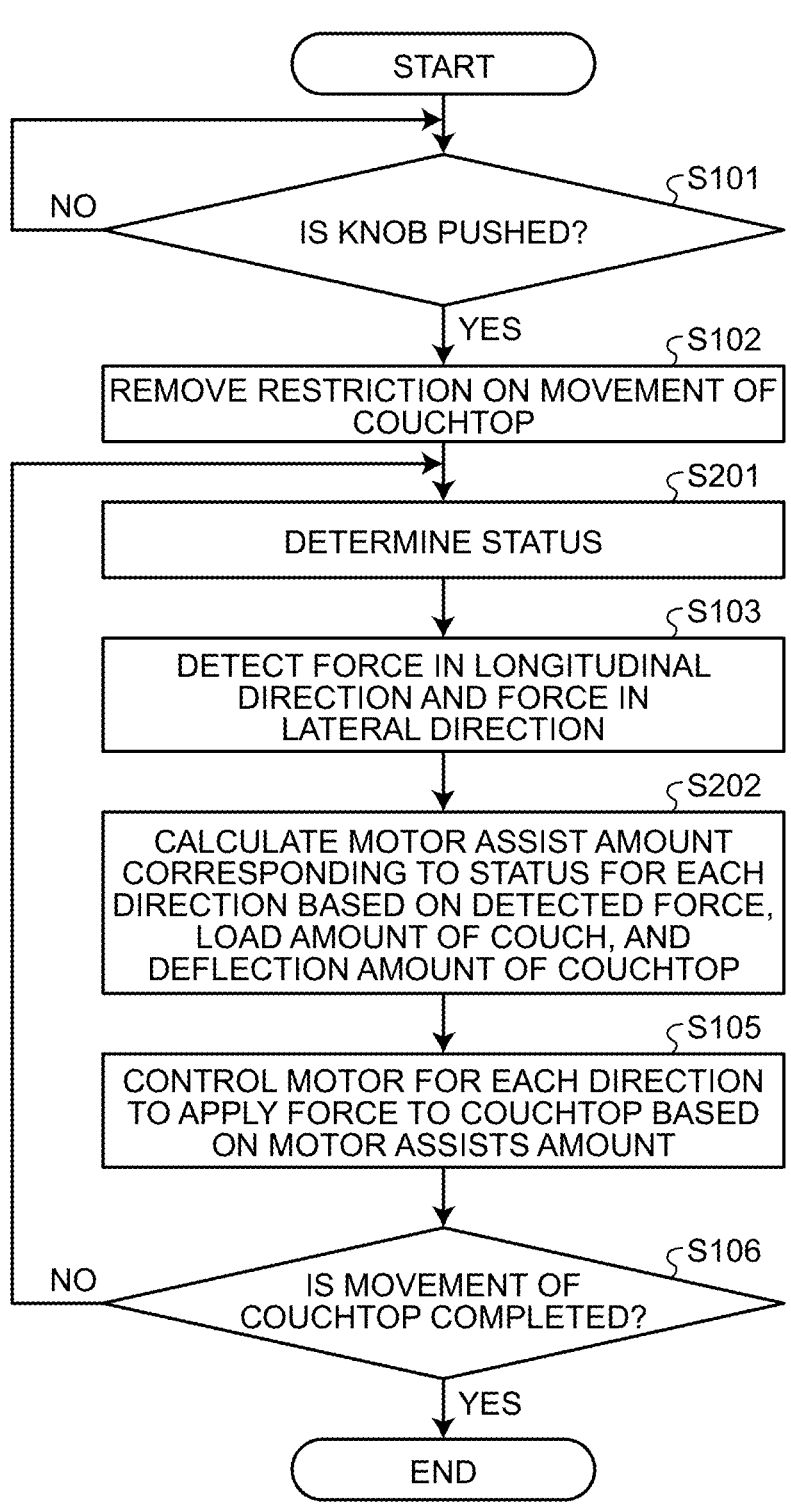
FIG. 18 is a flowchart indicating an example of a flow of processing executed by the couch device when assisting manual movement of the couchtop in the fifth embodiment.

FIG. 18 is a flowchart indicating an example of a flow of processing executed by the couch device when assisting manual movement of the couchtop in the fifth embodiment. The processing of steps S101 to S103, S105, and S106 illustrated in FIG. 18 is similar to the processing of steps S101 to S103, S105, and S106 illustrated in FIG. 12. The processing illustrated in FIG. 18 differs from the processing illustrated in FIG. 12 in respect that the processing of step S201 is executed between the processing of step S102 and the processing of step S103. Furthermore, the processing illustrated in FIG. 18 differs from the processing illustrated in FIG. 12 in respect that the processing of step S202 is executed instead of the processing of step S104. Thus, each processing of steps S201 and S202 will be described hereinafter.

First, the processing of step S201 will be described. As illustrated in FIG. 18, at step S201, the drive control function 152 determines whether it is in a status where fine adjustment of the position of the couchtop 11 is to be performed or a status where the couchtop 11 is to be moved at a relatively high speed.

For example, the drive control function 152 determines that it is in the status where fine adjustment of the position of the couchtop 11 is to be performed, when the signal output from the fine adjustment button 13e indicates ON. On the other hand, the drive control function 152 determines that it is in the status where the couchtop 11 is to be moved at a relatively high speed, when the signal output from the fine adjustment button 13e indicates OFF.

Note that the drive control function 152 may determine the various statuses at step S201 by other methods. For example, the X-ray diagnostic device 1 controls imaging by the imaging mechanism using exposure control signals for controlling the emission (exposure) of X-rays to the subject by the X-ray tube 21. Specifically, for example, the X-ray diagnostic device 1 sets the exposure control signal to ON to cause the X-ray tube 21 to emit X-rays. Furthermore, the X-ray diagnostic device 1 sets the exposure control signal to OFF to stop emission of the X-rays from the X-ray tube 21. Then, the drive control function 152 determines various statuses from the ON/OFF status indicated by the exposure control signal. Referring to a specific example, when the exposure control signal is acquired from the imaging mechanism and the acquired exposure control signal indicates ON, the drive control function 152 determines that it is in the status where fine adjustment of the position of the couchtop 11 is to be performed since it is in the fluoroscopic mode. On the other hand, when the exposure control signal indicates OFF, the drive control function 152 determines that it is in the status where the couchtop 11 is to be moved at a relatively high speed since it is not in the fluoroscopic mode.

Next, the processing of step S202 will be described. At step S202, the drive control function 152 calculates the motor assist amount corresponding to the status determined at step S201 for each of the longitudinal direction and the lateral direction of the couchtop 11 from the magnitude of the force applied to the couchtop 11 manually by the operator and one of the weight applied to the couchtop 11 and the deflection amount of the couchtop 11 acquired by the acquisition function 151.

For example, when determined at step S201 that it is in the status where fine adjustment of the position of the couchtop 11 is to be performed, the drive control function 152 calculates the motor assist amount at step S202 using "motor assist amount calculation algorithm A" that is for calculating a relatively small motor assist amount. This makes it possible to increase the ratio of the operation force of the operator contributing to the whole force applied to the couchtop 11 to move the couchtop 11.

Furthermore, when determined at step S201 that it is in the status where the couchtop 11 is to be moved at a relatively high speed, the drive control function 152 calculates the motor assist amount at step S202 using "motor assist amount calculation algorithm B" that is for calculating a relatively large motor assist amount. This allows the operator to move the couchtop 11 at a relatively fast speed.

In the fifth embodiment, the couch device 10 may include a speed sensor that detects the moving speed of the couchtop 11. The speed sensor is connected to the processing circuitry 150, and outputs a detection signal indicating the detected moving speed to the processing circuitry 150. Then, at step S201, the drive control function 152 determines whether the moving speed indicated by the detection signal from the speed sensor is equal to a predetermined threshold value or more to determine whether it is in the status where the moving speed of the couchtop 11 is fast or the status where the moving speed is slow. Then, when determined at step S201 that it is in the status where the moving speed of the couchtop 11 is fast, the drive control function 152 calculates the motor assist amount at step S202 using "motor assist amount calculation algorithm B" that is for calculating a relatively large motor assist amount. On the other hand, when determined at step S201 that it is in the status where the moving speed of the couchtop 11 is slow, the drive control function 152 calculates the motor assist amount at step S202 using "motor assist amount calculation algorithm A" that is for calculating a relatively small motor assist amount. In this manner, the drive control function 152 calculates the motor assist amount corresponding to the status of the moving speed of the couchtop 11.

By the method described above, the drive control function 152 determines the driving force corresponding to the status of the X-ray diagnostic device 1. Specifically, the drive control function 152 determines the driving force corresponding to the operation status of the fine adjustment button 13e of the X-ray diagnostic device 1. Furthermore, the drive control function 152 determines the driving force corresponding to the X-ray exposure status of the X-ray diagnostic device 1. Moreover, the drive control function 152 determines the driving force corresponding to the movement status of the couchtop 11 of the X-ray diagnostic device 1.

With the X-ray diagnostic device 1 and the couch device 10 according to at least one of the embodiments described above, it is possible to improve the operability of the operations for moving the couchtop 11.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray diagnostic device comprising:
an X-ray tube configured to emit X-rays to a subject;
an X-ray detector configured to detect X-rays transmitted through the subject;
a couchtop on which the subject is placed;
a drive mechanism configured to generate a driving force for moving the couchtop;
an input interface configured to accept an instruction operation from an operator regarding a movement of the couchtop; and
processing circuitry configured to acquire one of a weight applied to the couchtop and a deflection amount of the couchtop, and to determine the driving force to be generated by the drive mechanism based on one of the weight applied to the couchtop, the deflection amount of the couchtop, and on the instruction operation from the operator.

2. The X-ray diagnostic device according to claim 1, wherein the input interface includes a detection mechanism configured to detect at least one of a moving direction of the couchtop and a moving amount of the couchtop moved in the moving direction, and the input interface accepts at least one of the moving direction of the couchtop and the moving amount of the couchtop detected by the detection mechanism as the instruction operation from the operator regarding the movement of the couchtop.

3. The X-ray diagnostic device according to claim 1, wherein the input interface includes a control lever configured to accept the instruction operation from the operator.

4. The X-ray diagnostic device according to claim 3, wherein
the control lever includes a shaft and a knob provided at one end of the shaft, and
the input interface includes a detection mechanism configured to detect, as the instruction operation from the operator, at least one of a moving direction of the shaft and a magnitude of a force applied to the shaft by an operation of the operator.

5. The X-ray diagnostic device according to claim 4, wherein the detection mechanism is disposed around the shaft.

6. The X-ray diagnostic device according to claim 4, wherein the detection mechanism is provided at the other end of the shaft.

7. The X-ray diagnostic device according to claim 1, further comprising a restriction mechanism configured to restrict the movement of the couchtop,
wherein the input interface accepts a removal instruction from the operator for removing a restriction on the movement of the couchtop by the restriction mechanism.

8. The X-ray diagnostic device according to claim 1, wherein the processing circuitry determines the driving force based further on a tilt angle and a tilt direction of the couchtop.

9. The X-ray diagnostic device according to claim 1, wherein the processing circuitry determines the driving force corresponding to the operator.

10. The X-ray diagnostic device according to claim 1, wherein the processing circuitry determines the driving force corresponding to a status of the X-ray diagnostic device.

11. The X-ray diagnostic device according to claim 10, wherein the processing circuitry determines the driving force corresponding to an operation status of the input interface of the X-ray diagnostic device.

12. The X-ray diagnostic device according to claim 10, wherein the processing circuitry determines the driving force corresponding to an X-ray exposure status of the X-ray diagnostic device.

13. The X-ray diagnostic device according to claim 10, wherein the processing circuitry determines the driving force corresponding to a moving status of the couchtop of the X-ray diagnostic device.

14. A medical couch device comprising:
a couchtop on which a subject is placed;
a drive mechanism configured to generate a driving force for moving the couchtop;
an input interface configured to accept an instruction operation from an operator regarding a movement of the couchtop; and
processing circuitry configured to acquire one of a weight applied to the couchtop and a deflection amount of the couchtop, and to determine the driving force to be generated by the drive mechanism based on one of the weight applied to the couchtop, the deflection amount of the couchtop, and on the instruction operation from the operator.

15. The medical couch device according to claim 14, wherein the input interface includes a detection mechanism configured to detect at least one of a moving direction of the couchtop and a moving amount of the couchtop moved in the moving direction, and the input interface accepts at least one of the moving direction of the couchtop and the moving amount of the couchtop detected by the detection mechanism as the instruction operation from the operator regarding the movement of the couchtop.

16. The medical couch device according to claim 14, wherein the input interface includes a control lever configured to accept the instruction operation from the operator.

17. The medical couch device according to claim 16, wherein
the control lever includes a shaft and a knob provided at one end of the shaft, and
the input interface includes a detection mechanism configured to detect, as the instruction operation from the operator, at least one of a moving direction of the shaft and a magnitude of a force applied to the shaft by an operation of the operator.

18. The medical couch device according to claim 14, further comprising a restriction mechanism configured to restrict the movement of the couchtop,
wherein the input interface accepts a removal instruction from the operator for removing a restriction on the movement of the couchtop by the restriction mechanism.

19. The medical couch device according to claim 14, wherein the processing circuitry determines the driving force corresponding to the operator.

20. The medical couch device according to claim 14, wherein the processing circuitry determines the driving force corresponding to an operation status of the input interface, an X-ray exposure status of X-rays emittted to the subject, or a moving status of the couchtop.

* * * * *